United States Patent [19]
Chan et al.

[11] Patent Number: 5,990,318
[45] Date of Patent: Nov. 23, 1999

[54] SOLUBLE POLYESTER-SUPPORTED CHIRAL PHOSPHINES

[75] Inventors: Albert Sun-Chi Chan; Qing-Hua Fan, both of Kowloon, The Hong Kong Special Administrative Region of the People's Republic of China

[73] Assignee: The Hong Kong Polytechnic University, Kowloon, The Hong Kong Special Administrative Region of the People's Republic of China

[21] Appl. No.: 09/072,590

[22] Filed: Mar. 6, 1998

[51] Int. Cl.$^6$ .............................. C07F 9/02; C07F 15/02; C07C 229/72; C07D 207/00
[52] U.S. Cl. ......................... 548/412; 528/272; 528/287; 528/288; 556/19; 560/44; 564/15; 548/402
[58] Field of Search .............................. 560/44; 528/272, 528/287, 288; 548/402, 412; 564/15; 556/19

[56] References Cited

U.S. PATENT DOCUMENTS 4,705,895  11/1987  Okano et al. .............................. 564/15

OTHER PUBLICATIONS

Kazuo Ackiwa, "Catalytic Asymmetric Hydrogenations with Polymer Support Chiral Pyrrolidinephosphine–Rhodium Complexes", Chemistry Letters, pp. 905–908, 1978.
Wan et al., "Design and Synthesis of a Heterogeneous Asymmetric Catalyst", Nature, vol. 370, pp. 449–450, Aug. 11, 1994.
Han et al., "Soluble Polymer–Bound Ligand–Accelerated Catalysis: Asymmetric Dihydroxylation", J. Am. Chem. Soc., vol. 118, No. 32 pp. 7632–7633, 1996.
Bolm et al., "Asymmetric Dihydroxylation with MeO–Polyethyleneglycol–Bound Ligands", Angew. Chem. Int. Ed. Engl., vol. 36, No. 7, pp. 741–743, 1997.
Nagel et al., "Synthesis of Bis(phosphane) Palladium and Rhodium Complexes on a Polyethylene Oxide Grafted Polystyrene Matrix (TentaGel) and the Catalytic Behavior of the Rhodium Complexes", Chem. Ber., vol. 129, pp. 815–821, 1996.
Kitamura et al., "Practical Synthesis of Binap–Ruthenium(II) Dicarboxylate Complexes", J. Org. Chem, V. 57, pp. 4053–4054, 1992.
Holz et al., Strategies for Synthesis of Chiral Hydroxy Phosphines—A Class of Versatile Ligands and Ligand Precursors for Asymmetric Catalysis, Synthesis, pp. 983–1006, Sep. 1997.

Database Caplus on STN, Acc. No. 1997:488446, LIU et al., 'Water–soluble amphoteric pholymer–bound rhodium catalysts.' Book of Abstracts, 214th ACS National Meeting, Las Vegas, NV, Sep. 7–11 (1997) ORGN–042. American Chemical Society: Washington, D.C.

Database Caplus on STN, Acc. No. 1997:68843, Malmstroem et al., 'Synthesis, spectroscopic and catalytic properties of cationic Rh(i) complexes bound to phosphine functionalized water–soluble polymers.' J. Mol. Catal. A: Chem. (1997), 116(1–2), 237–245. (abstract).

Database Caplus on STN, Acc. No. 1995:538692, Malmstroem et al., 'Coupling of the Triphenylphosphine Moiety to Water–Soluble Polymers: A New Method to Achieve Water–Soluble Metal Phosphine Complexes.' Organometallics (1995), 14(5), 2593–6. (abstract).

Database Caplus on STN, Acc. No. 1987:118893, Parrinello et al., 'Platinum–catalyzed asymmetric hydroformylation with a ploymer–attached optically active phosphine ligand.' J. Org. Chem. (1986), 51(22), 4189–95. (abstract), 1987.

Database Caplus on STN, Acc. No. 1977:96552, Bernard et al., 'Comparison between homogeneous and supported catalysis in hydrogenation by rhodium–phosphine complexes. I. Homogeneous catalysts, and catalysts fixed on a soluble polymer.' Bull. Soc. Chim. Fr. (1976), (7–8, Pt. 2), 1163–7. (abstract), 1977.

Database Caplus on STN, Acc. No. 1976:462215, Schurig et al., 'A new class of catalysts.' Chemtech (1976), 6(3), 212–214. (abstract).

Primary Examiner—Gary Geist
Assistant Examiner—Brian J. Davis
Attorney, Agent, or Firm—Leydig, Voit & Mayer, Ltd.

[57] ABSTRACT

Novel soluble polyester-supported chiral phosphines have been prepared and have been used in the preparation of rhodium and ruthenium catalysts. Such polymer-supported catalysts show high catalytic activities and enantioselectivities. In the case of Ru(BINAP) catalyst supported on soluble polyester, the resulting catalysts were found to be more active than those of the corresponding homogeneous Ru(BINAP) catalysts in the asymmetric hydrogenation of 2-arylpropenoic acids. These soluble polyester-supported catalysts can be easily separated from the reaction mixture and then be reused without loss of activity and selectivity.

34 Claims, No Drawings

SOLUBLE POLYESTER-SUPPORTED CHIRAL PHOSPHINES

BACKGROUND OF THE INVENTION

1. Field of the Invention

The present invention relates to soluble polymer-supported chiral phosphines and, more particularly, relates to soluble polyester-supported chiral phosplines. The polyester-supported phosphine ligands have been used in the preparation of rhodium and ruthenium catalysts which are recyclable and useful in asymmetric catalysis.

2. Description of the Related Art

Polymer-supported catalysts have been attracting much attention due to their easy separation from the reaction mixture and the recyclability of the catalysts. The traditional polymer-supported catalysts used insoluble polymers or inorganic materials as support. The heterogenized catalysts can be separated easily from the reaction mixture via filtration or centrifugation at the end of catalytic reaction. However, the insoluble polymer-supported catalysts usually gave very low catalytic activity and enantioselectivity as compared to the corresponding free catalysts. The main reason is the restriction of the polymer matrix which results in the limited mobility and accessibility of the active sites. For example (see Achiwa, K. Chem. Lett., 1978, 905), a cross-linked polyalkyl methacrylate-supported Rh(BPPM) catalyst was found to catalyze the asymmetric hydrogenation of (Z)-acetamido-cinnamic acid to N-acetylphenylalanine in far lower e.e. (23%) as compared to the free Rh(BPPM) catalyst which gave 91% e.e.

Taking the above circumstances into consideration, extensive studies have been conducted in improving the catalytic activity and enantioselectivity of the polymer-supported catalysts. For example (see Nagel, U. et. al., Chem. Ber., 1996, 129, 815), the chiral phosphine DEGPHOS was supported on cross-linked polystyrene via polyethylene oxide chains which acted as "spacer" to enhance the mobility and accessibility of the catalytic species. The resulting polymer-supported bis(phosphane) rhodium catalyst showed about the same catalytic activity and enantioselectivity as the corresponding free catalyst in the asymmetric hydrogenation of dehydroamino acids. However, after one recycle, this polymer-supported catalyst abruptly lost activity. Another example (see Wan, K. T. et. al., Nature, 1994, 370, 449) is the immobilization of the water soluble organometallic complex, [Ru(BINAP-4SO$_3$Na)(benzene)Cl$_2$], in a thin ethylene glycol film on a high-surface area hydrophilic support such as silica or control-pore glass. The resulting catalyst was used to catalyze the hydrogenation of dehydronaproxen to give naproxen with similar enantioselectivity as the corresponding free Ru(BINAP) catalyst, but the catalytic activity was low (trim-over-frequencies were 40.7 hr$^{-1}$ vs 131.0 hr$^{-1}$).

Insoluble polymer-supported catalysts usually have low mechanical strength which may result in the change of the polymer structure, e.g. polystyrene beads collapse and shrink in polar solvents during catalytic reactions. The poor stability of the polymer-supported catalyst also results in the "leaching" of the noble metal from the support to the reaction solution. For these reasons the insoluble polymer-supported catalysts are not commercially attractive.

Another less known approach is to use a soluble polymer as the catalyst support. Recently, cinchona alkaloid type ligands were anchored on a soluble polyethylene glycol which showed similar catalytic activity and selectivity as compared to the corresponding free catalysts in the osmium-catalyzed asymmetric dihydroxylation of unfunctional olefins (see Han, J. and Janda, K. D., J. Am. Chem. Soc. 1996, 118, 7632; and Bolm C. and Gerlach, A., Angew. Chem. Int. Ed. Engl. 1997,36, 741). However, the separation of the polymer-supported ligands from the reaction mixtures is inconvenient and needed the use of a large amount of ether which is unsafe in industrial operation.

SUMMARY OF THE INVENTION

In our development of immobilized chiral phosphine ligands, we have developed a new type of polymer-supported catalyst which is, surprisingly, substantially superior to all known immobilized catalysts. The processes of this invention are distinctive as the asymmetric catalytic reaction can be carried out in an unhindered manner on a polymer support. The new technique of this invention combines the advantages of homogeneous and heterogeneous catalysis: high catalytic activity and stereoselectivity with easy separation of product from the reaction mixture and convenient recycling of the catalyst.

As a result, the present invention is highly useful for the preparation of a novel class of soluble polyester-supported chiral phosphines which are effective in asymmetric catalysis.

The present invention also relates to asymmetric hydrogenation reactions in which the catalyst thereof is a rhodium (I) or ruthenium(II) complex containing the said polymer-supported chiral phosphine ligand. In the case of soluble chiral polyester-supported Ru(BINAP), the said catalysts are more active as compared to the free Ru(BINAP) catalysts in the asymmetric hydrogenation of 2-arylpropenoic acids. The soluble polyester-supported catalysts can be easily separated from the reaction mixture and reused. In repeated experiments the polyester-supported catalysts were found to maintain the same activity and enantioselectivity after more than 10 recycles.

DETAILED DESCRIPTION OF THE INVENTION

As stated above, the present invention relates to a polymer-supported chiral phosphine in which the chiral phosphine ligand is anchored on a soluble polyester support. The transition metal complex containing the said polyester-supported chiral phosphine shows the same, or surprisingly even higher catalytic activity and enantioselectivity as compared to the corresponding free chiral catalysts in the asymmetric catalytic hydrogenation. The soluble polyester support useful in this invention can be prepared through polycondensation of diols and diacids or diacid halides.

The said diols include compounds represented by the formula:

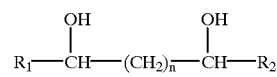

wherein:
i) R$_1$ and R$_2$ each independently represent alkyl or aryl radicals;
ii) n represents an integer from 0 to 12.

Examples of such diols include ethylene glycol, (1S,2S)- or (1R,2R)-1,2-diphenylethane-1,2-diol or its racemic form, diisopropyl L-tartrate, diethyl L-tartrate, 1,3-propanediol, (2S,4S)- or (2R,4R)-pentanediol or its racemic form, (1S,3S)- or (1R,3R)-l-phenylbutane-1,3-diol or its racemic form, (1S,3S)- or (1R,3R)-1,3-diphenylpropane-1,3-diol or its racemic form, 1,4-butanediol, (2S,4S)- or (2R,4R)-hexanediol or its racemic form, 1,8-octanediol, 1,9-nonanediol, 1,12-dodecanediol and the like.

The said diacids or diacid halides include alkyl, and aromatic diacids or diacid halides. Specific examples of such diacids or diacid halides include tartaric acid, adipoyl acid or its chloride, terephthaloyl acid or its chloride, isoplithaloyl acid or its chloride, 4,4'-biphenyldicarbonyl acid or its chloride, 4,4'-oxydi-(benzoyl chloride), 2,6-naphthalene-dicarbonyl chloride, and the like.

The chiral phosphines or their transition metal complexes are supported on the said soluble polyester support by methods well known in the art. For example, a copolymerization method in which the polyester-supported chiral phosphine is obtained by copolymerizing monomeric chiral phosphine ligand and diols with diacids or diacid halides, e.g.,

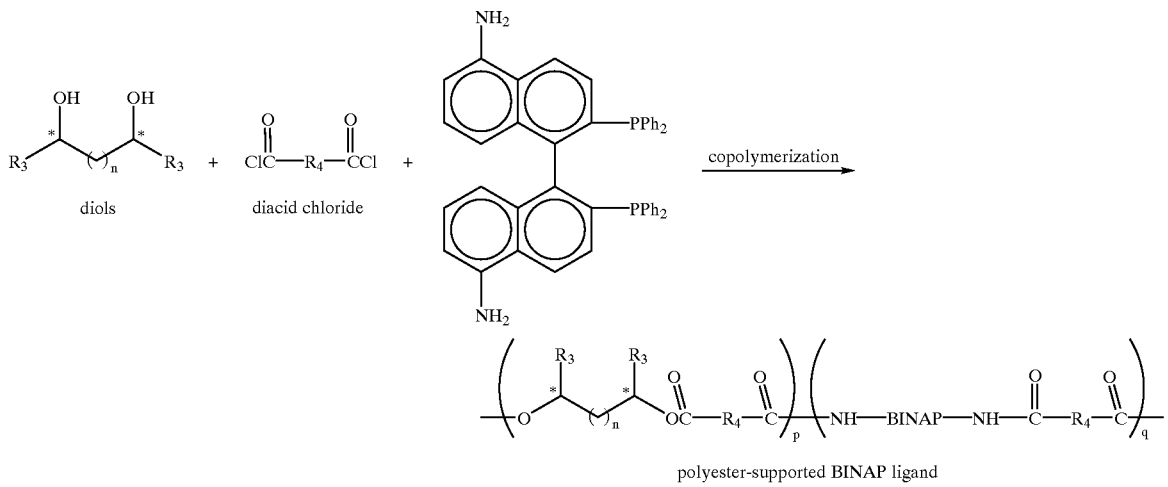

wherein:
i) p and q are the ratios of the number of the denoted monomeric units to the total number of monomeric units in the polymer; p is a decimal from 0.5 to 0.99; and q is a decimal determined according to the formula q=1-p;

ii) molecular weight is from 1000 to 300 000; and
iii) the diols and diacid chlorides are defined as above.

The soluble polyester-supported chiral phosphine can also be prepared by the reaction of a chiral phosphine with a soluble polyester, for example:

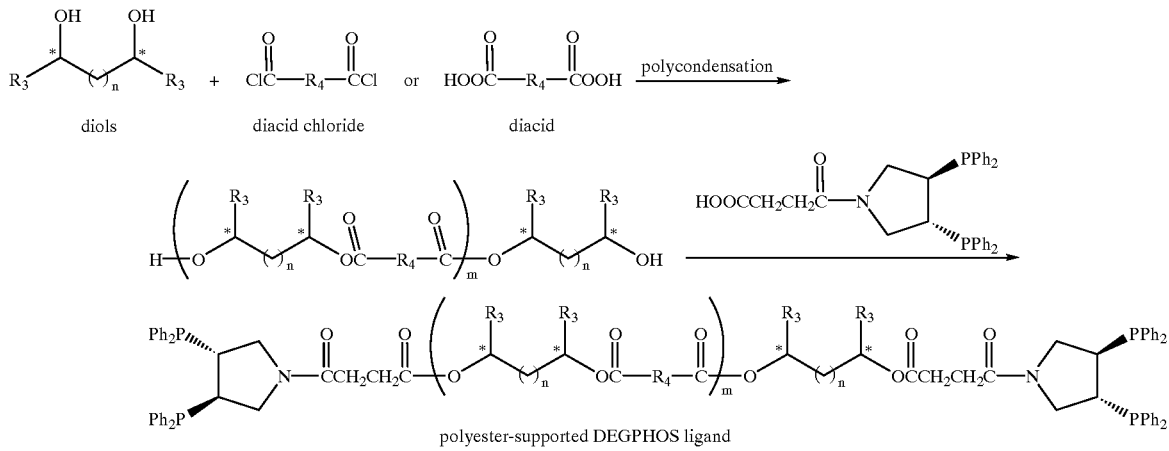

wherein:

i) m represents an integer from 10 to 200;
ii) the diols and diacid chlorides or diacids are defined as above.

The chiral phosphines useful in the present invention include chiral hydroxyphosphines (see Holz, J., Quirmbach, M. and Borner, A., *Synthesis*, 1997, 983), chiral aminophosphines (e.g. 5,5'-diamino BINAP, U.S. Pat. No. 4,705,895) and the like. Examples of suitable chiral phosphines include:
(a) optically active bisphosphine binaphthyl compounds of the formula:

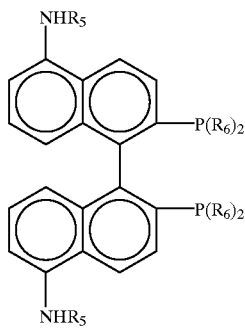

wherein:

i) $R_5$ represents a hydrogen atom, a straight or branched chain alkyl group having 1 to 6 carbon atoms, or a straight or branched chain alkoxy group having from 1 to 6 carbon atoms, or a carbocyclic aromatic group having from 6 to 14 carbon atoms, or an alkyl or alkoxy group as defined above which is substituted by a carbocyclic aromatic group as defined above.

ii) $R_6$ is chosen from the following groups:

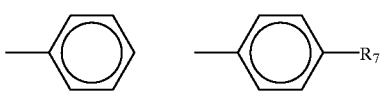

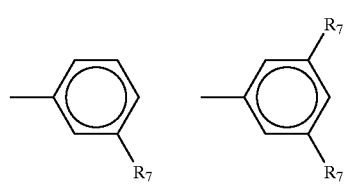

wherein $R_7$ is selected from the group consisting of a straight or branched chain alkyl group having 1 to 6 carbon atoms, and a straight or branched chain alkoxy group having from 1 to 6 carbon atoms;

(b) optically active bisphosphine biphenyl or bipyridyl compounds of the formula:

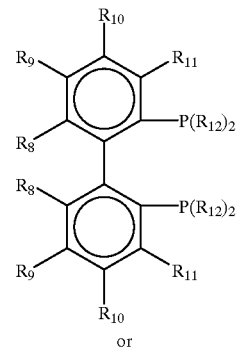

or

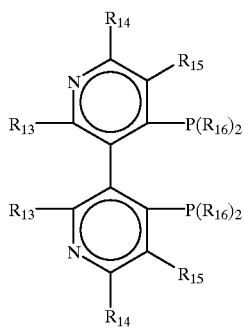

wherein:
i) $R_8$ and $R_{13}$ are independently selected from the group consisting of straight or branched chain alkyl groups having 1 to 6 carbon atoms, and straight or branched chain alkoxy groups having from 1 to 6 carbon atoms;
ii) $R_9$, $R_{10}$, and $R_{11}$ are independently selected from the group consisting of hydrogen atoms, hydroxy groups, amino groups, straight or branched chain alkyl group having 1 to 6 carbon atoms, and straight or branched chain alkoxy group having from 1 to 6 carbon atoms, with the proviso that at least one of $R_9$, $R_{10}$, and $R_{11}$ is a hydroxy group or an amino group;
iii) $R_{14}$ and $R_{15}$ are independently selected from the group consisting of hydrogen atoms, hydroxy groups, amino groups, straight or branched chain alkyl group having 1 to 6 carbon atoms, and straight or branched chain alkoxy group having from 1 to 6 carbon atoms, with the proviso that at least one of $R_{14}$ and $R_{15}$ is a hydroxy group or an amino group;
iv) $R_{12}$ and $R_{16}$ are independently selected from the following groups:

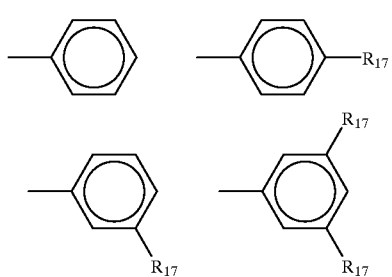

wherein $R_{17}$ is selected from the group consisting of a straight or branched chain alkyl group having 1 to 6 carbon atoms, and a straight or branched chain alkoxy group having from 1 to 6 carbon atoms;

(c) optically active bisphospine ferocenyl compounds of the formula:

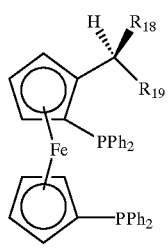

wherein:

i) $R_{18}$ is selected from the group consisting of a straight or branched chain alkyl group having 1 to 6 carbon atoms, and a straight or branched chain alkoxy group having from 1 to 6 carbon atoms; and ii) $R_{19}$ is selected from the group consisting of hydroxy groups and substituents of formula $N(R_{20})_2$, said substituent of formula $N(R_{20})_2$ being selected from the following groups:

NMe(CH$_2$)$_2$OH, NH(CH$_2$)$_2$OH, N[(CH$_2$)$_2$OH]$_2$,

NMeCH(CH$_2$OH)$_2$, NH[CH$_2$CMe$_2$OH], NH(CH$_2$)$_3$OH,

NH(CH$_2$)$_2$O(CH$_2$)$_2$OH, NMeC(CH$_2$OH)$_3$, 1,2-NH—C$_6$H$_4$—OH,

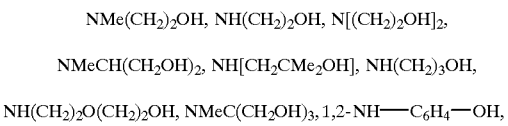

(d) optically active bisphosphine pyrrolidinyl compounds of the formula:

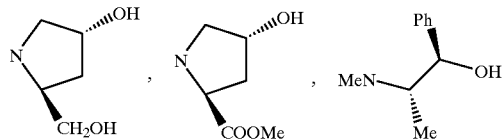

wherein $R_{21}$, $R_{22}$, $R_{23}$ and $R_{24}$ are independently selected from the group consisting of cycloalkyl groups having from 4 to 8 carbon atoms and aryl groups, said aryl groups being selected from the following groups:

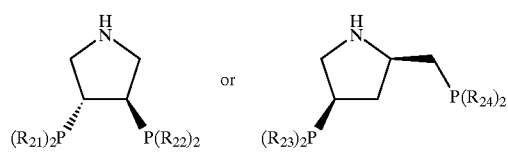

-continued

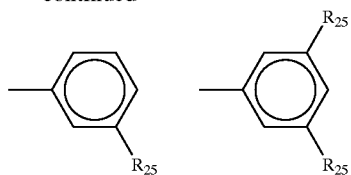

wherein $R_{25}$ is selected from a group consisting of straight or branched chain alkyl groups having 1 to 6 carbon atoms, and straight or branched chain alkoxy groups having from 1 to 6 carbon atoms; and (e) optically active bisphosphine compounds of the formula:

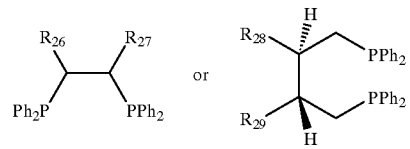

wherein:

i) $R_{26}$ and $R_{28}$ are the same or different and each represents a group of formula —(CH$_2$)$_r$OH wherein r is an integer of from 0 to 8;

ii) $R_{27}$ is the same as $R_{26}$ or is selected from the group consisting of a hydrogen atom, straight or branched chain alkyl groups having 1 to 6 carbon atoms, and straight or branched chain alkoxy groups having from 1 to 6 carbon atoms; and iii) $R_{29}$ is the same as $R_{28}$ or is selected from the group consisting of hydrogen atoms, straight or branched chain alkyl groups having 1 to 6 carbon atoms, and straight or branched chain alkoxy groups having from 1 to 6 carbon atoms.

For the purposes of this invention, the polyester-supported catalyst can be prepared in-situ by the reaction of the said soluble polyester-supported chiral phosphine ligand (pp) with [Ru(cymene)Cl$_2$]$_2$ in a suitable organic solvent system such as a mixture of methanol-toluene, ethanol-THF, methanol-benzene, methanol-dichloromethane, and the like to produce the polyester-supported ruthenium(II) complexes [(PP)(cymene)Cl$_2$]. The polyester-supported catalyst, Ru(PP)(OAc)$_2$ can also be prepared according to the method described by Noyori et al (J. Org. Chem., 1992, 57, 4053), and the acetate anion can be replaced with sodium acetoacetate to afford the polyester-supported catalyst Ru(pp)(acac)$_2$. Alternatively, the said soluble polyester-supported chiral phosphine ligand (PP) can be reacted with [Rh(COD)Cl]$_2$ to give polyester-supported catalyst Rh(PP)(COD)Cl in-situ. The coordination ligand Cl can be replaced with BF$_4^-$ or other non-coordinating or weakly coordinating anions such as ClO$_4^-$, PF$_6^-$, and the like.

For the purposes of this invention, the said polyester-supported Ru(PP) or Rh(PP) complexes can be used as catalysts in the hydrogenation of 2-arypropenoic acids such as 2-(6-methoxy-2-naphthyl)propenoic acid, 2-(p-isobutylphenyl)propenoic acid, or α-amidoacrylic acids and esters such as (Z)-α-benzamidocinnamic acid, (Z)-α-(benzamido)-β-(4-hydroxy-3-methoxy-phenyl)acrylic acid in a suitable organic solvent systems such as methanol, THF, or methanol-toluene, MeOH-THF, and the like.

The polyester-supported Ru(PP) or Rh(PP) catalysts can catalyze the asymmetric hydrogenation in a homogeneous manner. The polyester-supported catalysts of the present

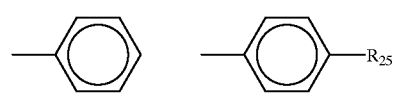

invention give high catalytic activities and enantioselectivities as compared with the corresponding free catalysts. Upon the completion of the reaction, the polyester-supported catalysts can be easily separated from the reaction mixture through simple methods such as temperature change, selective precipitation and differential solubility. In the case of Ru(BINAP) catalyst supported on soluble polyester, the resulting catalysts were found to be more active than those of the corresponding homogeneous Ru(BINAP) catalysts in the asymmetric hydrogenation of 2-arylpropenoic acids. The soluble polyester-supported catalysts can be easily separated (from the reaction mixture upon the addition of cold methanol) and reused. In repeated experiments the polyester-supported catalysts were found to maintain the same activity and enantioselectivity after more than 10 recycles.

The following examples of experiments are provided to illustrate but not to limit the scope of the usefulness of this invention. In the said examples, the following abbreviations are used: PP=soluble polyester-supported chiral phosphine ligand, DMF=N, N'-dimethylformamide, MeOH=methanol, THF=tetrahydrofuran, COD=cyclooctadiene, e.e.= enantiomeric excess, DCC=dicyclohexylcarbodiimide, DMAP=4-N, N'-dimethylaminopyridine, 5,5'-diamino BINAP=5,5'-diamino-2,2'-bis(diphenylphosphino)-1,1'-binaphthyl, BINAP-NH$_2$=5,5'-diamino BINAP, dehydronaproxen=2-(6'-methoxy-2'-naphthyl)propenoic acid, BPPM=N-substituted (2R, 4R)-4-diphenylphosphino-2-[(diphenylphosphino)ethyl]pyrrolidine, DEGPHOS=N-substituted (3R,4R)-bis(diphenylphosphino)pyrrolidine.

EXAMPLE 1

Preparation of Soluble Chiral Polyester-Supported (S)-BINAP Ligand

In a three-necked flask, which was equipped with a stirring bar, a solid chemical transferring funnel, and a reflux condenser, was added 1.015 g (9.76 mmol) 2S,4S-pentanediol, 2.0 mL pyridine and 30 mL 1,2-dichloroethane. To this mixture was added portionwise 2.02 g (9.95 mmol) of terephthaloyl chloride in a period of 10 min. A solution of 150 mg (0.23 mmol) (S)-5,5'-diamino-BINAP in 10 mL 1,2-dichloroethane was further added dropwise. The reaction mixture was heated at reflux temperature for 8 h under nitrogen, and then was poured into a flask containing 300 mL of methanol. The precipitated polymer was collected by filtration. The polymer was dissolved with 10 mL dichloromethane and to this mixture was slowly added 100 mL methanol under stirring. The precipitated polymer was collected, washed with methanol, and dried in vacuo to give 2.3 g polyester-supported BINAP ligand (93.5% theoretical yield):

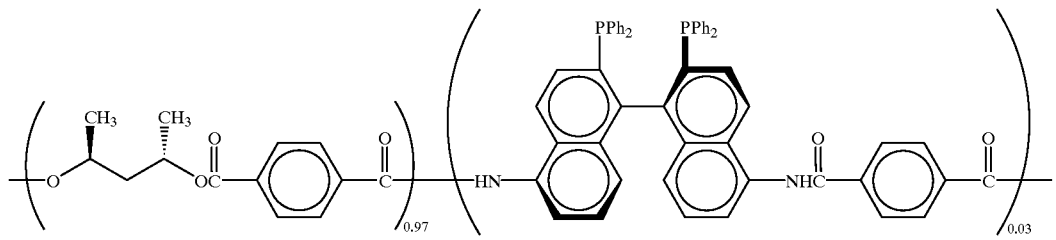

The analytical data for this new material are as follows:
Molecular weight (M$_w$)=10540 (on the base of polystyrene calibration); amount of BINAP moieties=5.65 g per 100 g polymer[determined by $^1$H NMR (400MHz)]; $[\alpha]_D^{20}$= 245.0 (c 0.20, CHCl$_3$); IR (film): 2986, 2934, 1717(C=O), 1274, 1118, 1102, 1018, 729 cm$^{-1}$; $^1$H NMR (400 MHz, CDCl$_3$): 1.42 (d, J=6.2 Hz, 6H), 2.11 (t, J=6.2Hz, 2H), 5.30 (sextet, J=6.2 Hz, 2H), 8.00 (s, 4H), [for BINAP moiety: 6.74 (d, J=8.50 Hz, 2H), 6.97~7.22 (m, 22H), 7.51 (d, J=9.36 Hz, 2H)] ppm; $^{31}$P NMR (160 MHz, CDCl$_3$): −16.7 ppm; Element analysis: found C 66.07, H 5.78, N<0.30, calculated C 67.63, H 5.88, N0.26.

EXAMPLE 2

Preparation of Soluble Chiral Polyester-Supported (R)-BINAP Ligand

In a three-necked flask, which was equipped with a stirring bar, a solid chemical transferring funnel, and a reflux condenser, was added 312 mg (3.0 mrnol) 2S,4S-pentanediol, 0.5 mL pyridine and 10 mL 1,2-dichloroethane. To this mixture was added portionwise 620 mg (3.05 mmol) of terephthaloyl chloride in a period of 10 min. A solution of 50 mg (0.077 mmol) (R)-5,5'-diamino-BINAP in 5 mL 1,2-dichloroethane was further added dropwise. The reaction mixture was heated at reflux temperature for 8 h under nitrogen, and then was poured into a flask containing 100 mL of methanol. After the work-up as described in Example 1, 680 mg of polyester-supported BINAP ligand was obtained (89.5% theoretical yield):

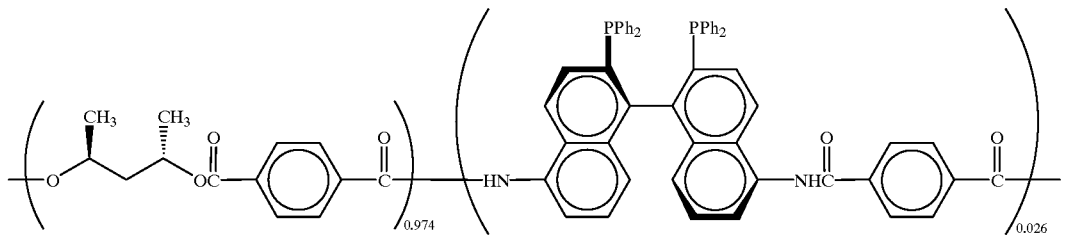

The analytical data for this new material are as follows:

Molecular weight ($M_W$)=10311 (on the base of polystyrene calibration); amount of BINAP moieties=4.88 g per 100 g of polymer[determined by $^1$H NMR (400 MHz)]; $[\alpha]_D^{20}$= 275.0 (c 0.20, CHCl$_3$); $^{31}$P NMR (160 MHz, CDCl$_3$): −16.7 ppm.

EXAMPLE 3
Preparation of Soluble Racemic Polyester-Supported (S)-BINAP Ligand In a three-necked flask, which was equipped with a stirring bar, a solid chemical transferring flinnel, and a reflux condenser, was added 312 mg (3.0 mmol) racemic 2,4-pentanediol, 0.5 mL pyridine and 10 mL 1,2-dichloroethane. To this mixture was added portionwise 620 mg (3.05 mmol) of terephthaloyl chloride in a period of 10 min. A solution of 50 mg (0.077 mmol) (S)-5,5'-diamino-BINAP in 5 mL 1,2-dichloroethane was further added dropwise. The reaction mixture was heated at reflux temperature for 8 h under nitrogen, and then was poured into a flask containing 100 mL of methanol. After the work-up as described in Example 1, 450 mg of polyester-supported BINAP ligand was obtained (59.5% theoretical yield):

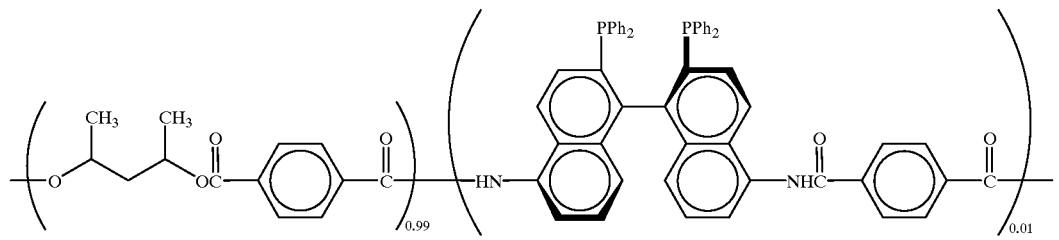

The analytical data for this new material are as follows:

Molecular weight ($M_W$)=3445 (on the base of polystyrene calibration); amount of BINAP moieties=4.98 g per 100 g of polymer[determined by $^1$H NMR (400 MHz)]; $[\alpha]_D^{20}$=15.0 (c 0.20, CHCl$_3$); $^{31}$P NMR (160 MHz, CDCl$_3$): −16.7 ppm.

EXAMPLE 4

Preparation of Soluble Chiral Polyester-Supported DEGPHOS Ligand (1) Synthesis of (3R, 4R)-N-(4-carboxybutanoyl)-3,4-bis(diphenyl phosphanyl)pyrrolidine. In a 50-mL flask, which was equipped with a stirring bar, was charged with 100 mg (0.228 mmol) of (3R, 4R)-3,4-bis(diphenylphosphanyl)pyrrolidine, 114 mg (1.14 mmol) of glutaric acid and 20 mL dichloromethane. The reaction mixture was then stirred overnight at ambient temperature. After washing with water, the dichloromethane phase was filtered through MgSO$_4$. Addition of diethyl ether to the dichloromethane phase afforded 120 mg of (3R, 4R)-N-(4-carboxybutanoyl)-3,4-bis(diphenylphosphanyl)pyrrolidine as yellow crystals by filtration (98.0% theoretical yield).

(2) Synthesis of soluble chiral OH-terminating polyester. In a three-necked flask, which was equipped with a stirring bar, a solid chemical transferring funnel, and a reflux condenser, was added 2.08 g (0.02 mol) 2S,4S-pentanediol, 4.0 mL pyridine and 30 mL 1,2-dichloroethane. To this mixture was added portionwise 3.8 g (0.0187 mol) of terephthaloyl chloride in a period of 10 min. The reaction mixture was heated at reflux temperature for 8 h under nitrogen, and then was poured into a flask containing 300 mL of methanol. The precipitated polymer was collected by filtration. The precipitated polymer was collected, washed with methanol, and dried in vacuo to give 4.28 g chiral OH-terminating polyester (94.5% theoretical yield). [Molecular weight ($M_W$)=4200 (on the base of polystyrene calibration)]

(3) Preparation of polyester-supported DUGPHOS ligand. DCC (40 mg, 0.194 mmol) was added to a mixture of the above OH-terminating polyester (Mw=4200, 0.390 g, ~0.186 mmol OH), (3R, 4R)-N-(4-carboxybutanoyl)-3,4-bis(diphenylphosphanyl)pyrrolidine (120 mg, 0.223 mmol), and DMAP (5 mg, 0.041 mmol) in dichloromethane (20 mL). The reaction mixture was stirred for 12 h at ambient temperature and the urea precipitate was removed by filtration. Methanol was then slowly added to the resulting filtrate under stirring, and the precipitated polyester-supported DEGPHOS ligand was then isolated by filtration, and washed with cold methanol and dried in vacuo to give 380 mg polymeric DEGPHOS ligand (96% theoretical yield):

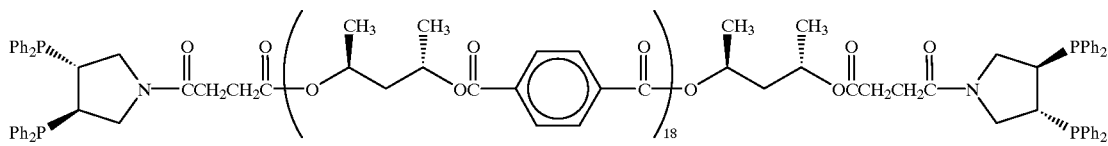

The analytical data for this new material are as follows:

$^1$H NMR (400 MHz, CDCl$_3$): 2.42~2.45 (m, 2H), 2.61~2.65 (m, 2H), 2.89~2.98 (m, 2H), 7.14~7.18 (m, 4H), 7.22~7.26 (m, 4H), 7.31~7.38 (m, 12H) and for polyester moiety: 1.47 (d, J=7.6 Hz, 6H), 2.11 (m, 2H), 5.30 (m, 2H), 8.00 (m, 4H) ppm; $^{31}$P NMR (160 MHz, CDCl$_3$): -12.6, -12.8 (dd, J$_1$=8.10 Hz, J$_2$=35.96 Hz); amount of DEGPHOS moieties=16.5 g per 100 g of polymer[determined by $^1$HNMR (400 MHz).

ambient temperature and the urea precipitate was removed by filtration through celite. Cold methanol was slowly added to the resulting filtrate under stirring, and the precipitated polymer-supported BPPM phosphine ligand was then isolated by filtration, and washed with absolute methanol and dried in vacuo to give 1.03 g of polymeric BPPM ligand (94% theoretical yield):

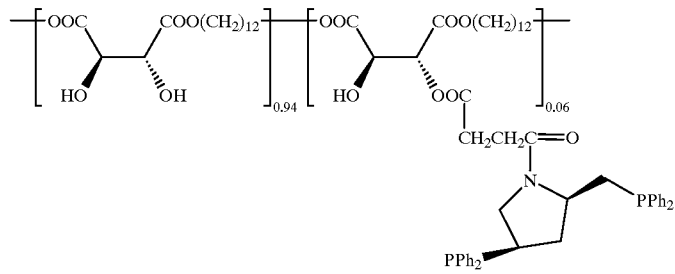

EXAMPLE 5
Preparation of Soluble Poly(alkylene tartrate)-Supported BPPM Ligand (1) Synthesis of N-(4-carboxybutanoyl)-3,4-bis (diphenylphosphanyl) pyrrolidine. In a 50-mL flask, which was equipped with a stirring bar, was charged 100 mg (0.221 mmol) of (2R, 4R)-4-(diphenyl- phosphino-2-[(diphenyl-phosphino)methyl]pyrrolidine, 114 mg (1.14 mmol) of glutaric acid anhydride and 20 mL dichloromethane. The reaction mixture was then stirred overnight at ambient temperature. After washing with water, the dichloromethane phase was filtered through MgSO$_4$. Addition of diethyl ether to the dichloromethane phase afforded 120 mg of (4R, 2R)-N-(4-carboxybutanoyl)-4-(diphenyl-phosphino-2-[(diphenylphosphino)methyl]pyrrolidine as yellow crystals by filtration (98% theoretical yield).

(2) Synthesis of poly(alkylene tartrate). In a two-neck 100 mL flask, which was equipped with a condenser, a vacuum distillation head and a stirring bar, was charged 1,12-dodecanediol (10.0 g, 49.4 mmol), L-tartaric acid (7.35 g, 49.0 mmol) and SnCl$_2$.2H$_2$O (150 mg). The mixture was heated under nitrogen atmosphere to 130° C. for 2 h, and the pressure was then reduced to about 5 mm Hg and the mixture was heated for another 2 h. The crude polymer thus obtained was dissolved in dichloromethane, filtered and precipitated from cold methanol. The precipitated polymer was washed with methanol and then dried over P$_2$O$_5$ in vacuo to give 15.0 g chiral polyester(96% theoretical yield).

(3) Preparation of polyester-supported BPPM ligand. DCC (40 mg, 0.194 mmol) was added to a mixture of the above poly(alkylene tartrate) (1.0 g), (4R, 2R)-N-(4-carboxybutanoyl)-4-(diphenylphosphino)-2-[(diphenylphosphino)methyl]pyrrolidine (120 mg, 0.217 mmol), and DMAP (5 mg, 0.041 mmol) in dichloromethane (20 mL). The reaction mixture was stirred for 12 h at The analytical data for this new material are as follows:
Molecular weight (M$_w$) 8850 (on the base of polystyrene calibration); amount of BPPM moieties=8.52 g per 100 g of polymer [determined by $^1$H NMR (400 MHz)]; $^1$H NMR (400 MHz, CDCl$_3$): 2.05~2.54 (m, 8H), 2.85~2.9 (m, 2H), 3.49~3.54 (m, 2H), 7.26~7.52 (m, 20H), [poly(alkylene tartrate): 1.25~1.31 (m, 20H), 1.64~1.68 (m, 4H), 3.29 (s, 2H), 4.21~4.24 (m, 4H), 4.52 (s, 2H) ppm; $^{31}$P NMR (160 MHz, CDCl$_3$): -7.78, -10.50, -24.93 ppm.

EXAMPLE 6
Asymmetric Hydrogenation of Dehydronaproxen Catalyzed by Soluble Chiral Polyester-Supported [Ru(BINAP)(cymene)Cl$_2$] Catalyst (1) Preparation of polyester-supported [Ru(BINAP)(cymene)Cl$_2$] catalyst. A mixture of 500 mg polyester-supported BINAP ligand (from Example 1) and 12 mg (1.96×10$^{-2}$ mmol) of [Ru(cymene)Cl$_2$]$_2$ in 10 mL toluene/MeOH (4/1, v/v) was magnetically stirred under nitrogen atmosphere at about 50~60° C. for 60 min. The reaction mixture was poured into a flask containing 150 mL of cool methanol, and the precipitated polymer-supported Ru(BINAP) catalyst was collected by filtration. The catalyst thus obtained was dissolved in 5 mL dichloromethane. To this mixture was slowly added 100 mL cold methanol under stirring. The precipitated catalyst was collected, washed with cool methanol, and dried in vacuo to give 501.5 mg polyester-supported Ru(BINAP) catalyst (98.0% theoretical yield). [$^{31}$P NMR (400 MHz, CDCl$_3$): 38.6 (d J=63.0 Hz), 24.2 (d 60.6 Hz) ppm; Element analysis: found C 66.33, H 5.88, N<0.30; calculated C 67.90, H 5.94, N 0.26.]

(2) Asymmetric hydrogenation. A 50 mL autoclave with a magnetic stirring bar was charged with 8 mg of the above polyester-supported Ru(BINAP) catalyst, 30 mg (0.126 mmol) of dehydronaproxen, 12.8 mg (0.126 mmol) of triethylamine, and 6.0 mL of toluene-MeOH (3:2, v/v). The autoclave was then pressurized with hydrogen to 110 kg/cm$^2$ and the mixture was stirred at 0° C. for 15 h. A portion of the reaction mixture was analyzed by HPLC to determine the product composition. Complete conversion (100%) of the starting material to the hydrogenation product and 94.4% e.e. of naproxen were observed. Activated carbon (4 mg) was added to the solution and the mixture was stirred for 15 min. After filtration, the organic solvent was evaporated to give a white solid of (S)-naproxen (29.4 mg), 98.0% yield and 94.4% e.e.

The products were analyzed by HPLC using a SUMICHIRAL OA-2500 column (Produced by Sumika Chemical Analysis Service, Ltd. Scientific Instruments Div. Chromatography Group): eluent=6×10$^{-3}$ M NH$_4$OAc of MeOH solution; flow rate=1.2 mL/min; $t_R$(R)=14.63, $t_R$(S)=17.33, and $t_R$(N2)=14.82 min.

EXAMPLE 7

Asymmetric Hydrogenation of Dehydronaproxen Catalyzed by Soluble Chiral Polyester-Supported Ru(BINAP)(OAc)$_2$ Catalyst (1) Preparation of polyester-supported Ru(BINAP)(OAc)$_2$ catalyst. A mixture of 50 mg polyester-supported BINAP ligand (from Example 1) and 0.98 mg (1.96×10$^{-3}$ mmol) of [Ru(benzene)Cl$_2$]$_2$ in 4 mL dried DMF was heated to 150° C. under nitrogen atmosphere for 10 min. After the reaction mixture was cooled to ambient temperature, a mixture of 50 mg (0.6 mmol) sodium acetate (NaOAc) and 0.5 mL methanol was added. The mixture was stirred for another 30 min at ambient temperature. The reaction mixture was poured into a flask containing 50 mL of cold methanol, and the precipitated polymer-supported Ru(BINAP) catalyst was collected by filtration. The catalyst thus obtained was dissolved in 2 mL dichloromethane. To this mixture was slowly added 50 mL cold methanol under stirring. The precipitated catalyst was collected, washed with cool methanol, and dried in vacuo to give 48 mg polyester-supported Ru(BINAP)(OAc)$_2$ catalyst (94.0% theoretical yield). [$^{31}$P NMR (160 MHz, CDCl$_3$): 65.4 ppm].

(2) Asymmetric hydrogenation. The hydrogenation was carried out via the same procedure as in example 6 using the above polyester-supported Ru(BINAP)(OAc)$_2$ catalyst to give the product (S)-naproxen, 97.9% yield and 94.0% e.e.

EXAMPLE 8

Asymmetric Hydrogenation of Dehydronaproxen Catalyzed by Polyester-Supported [Ru(BINAP)(cymene)Cl$_2$] Catalyst Prepared in situ A 50 mL autoclave with a magnetic stirring bar was charged with 4 mg polyester-supported BINAP ligand (from Example 1), 0.096 mg (1.57×10$^{-4}$ mmol) of [Ru(cymene)Cl$_2$]$_2$ and 2.5 mL of toluene/MeOH (3:2, v/v), and the mixture was premixed for 20 min to afford the in situ catalyst. Fifteen mg of dehydronaproxen and 8 μL of NEt$_3$ was then added. The autoclave was then pressurized with hydrogen to 110 kg/cm$^2$ and the mixture was stirred at 0° C. for 15 h. A portion of the reaction mixture was analyzed by HPLC to determine the product composition. Complete conversion (100%) of the starting material to the hydrogenation product and 94.0% e.e. of naproxen were observed. Activated carbon (4 mg) was added to the solution and the mixture was stirred for 15 min. After filtration, the organic solvent was evaporated to give a white solid of (S)-naproxen (29.4 mg), yield 98.0% and 94.0% e.e.

EXAMPLE 9

Asymmetric Hydrogenation of Dehydronaproxen Catalyzed by Polyester-Supported [Ru(BINAP)(cymene)Cl$_2$] Catalyst Prepared in situ This example illustrates the effect of reaction temperature on the enantioselectivity:

The hydrogenation was carried out via a similar procedure as in example 8 by using the in-situ catalyst prepared in Example 8. The results are summarized in Table 1:

TABLE 1

| Temperature (° C.) | 60 | 20 | 0 |
|---|---|---|---|
| Reaction time (h) | 2 | 4 | 10 |
| E.e. (%) | 80.5 | 87.2 | 94.2 |
| Conv. (%) | 100 | 96.4 | 98.6 |

EXAMPLE 10

Asymmetric Hydrogenation of Dehydronaproxen Catalyzed by Polyester-Supported [Ru(BINAP)(cymene)Cl$_2$] Catalyst Prepared in situ This example illustrates the effect of solvent on the enantioselectivity of the asymmetric hydrogenation of dehydronaproxen by using the polyester-supported [Ru(BINAP)(cymene)Cl$_2$] catalyst and the free [Ru(BINAP-NH$_2$)(cymene)Cl$_2$] catalyst:

A 50 mL autoclave with a magnetic stirring bar was charged with 4 mg polyester-supported BINAP ligand (from Example 2), 0.096 mg (1.57×10$^{-4}$ mmol) of [Ru(cymene)Cl$_2$]$_2$ and 2.5 mL of CH$_2$Cl$_2$/MeOH, and the mixture was premixed for 20 min to afford the in situ catalyst, and 15 mg (0.063 mmol) of dehydronaproxen, 6.4 mg (0.063 mmol) of triethylamine and 2.5 mL was then added. The autoclave was then pressurized with hydrogen to 69.0 kg/cm$^2$ and the mixture was stirred at 25° C. for 12 h. The [Ru(BINAP-NH$_2$)(cymene)Cl$_2$]-catalyzed asymmetric hydrogenation of dehydronaproxen was carried out via a similar procedure using [Ru(BINAP-NH$_2$)(cymene)Cl$_2$] instead of the polyester-supported [Ru(BINAP)(cymene)Cl$_2$]. The results are summarized in Table 2:

TABLE 2

| MeOH/CH$_2$Cl$_2$ (v/v) | 3:2 | 2:3 | 1:4 | 1:9 | 1:49 | 0:1 |
|---|---|---|---|---|---|---|
| E.e. (%)$^a$ | 85.4 | 83.5 | 82.4 | 81.8 | 69.0 | 31.3 |
| E.e. (%)$^b$ | 86.9 | 86.3 | 85.4 | 84.6 | 75.8 | 39.0 |

$^a$Catalyst = [Ru(BINAP—NH$_2$)(cymene)Cl$_2$];
$^b$Catalyst = polyester-supported [Ru(BINAP)(cymene)Cl$_2$]. 100% conversion was observed in all cases.

EXAMPLE 11

Asymmetric Hydrogenation of Dehydronaproxen Catalyzed Polyester-Supported [Ru(BINAP)(cymene)Cl$_1$] Catalyst Prepared in situ This example illustrates the comparison between polyester-supported Ru(BINAP) catalysts and the related free Ru(BINAP) catalysts:

The hydrogenation was carried out via the same procedure as in the above example 8, using in situ polyester-supported catalyst prepared in accordance with the procedure of Example 8 or the related free Ru(BINAP) catalysts. The reaction conditions and the results are summarized in Table 3:

TABLE 3

| Entry | Catalysts | Time, h | E.e., %[b] | Conv., %[b] |
|---|---|---|---|---|
| 1 | Poly-Cat. | 12 | 93.6 | 97.4 |
| 2 | Poly-Cat. | 12 | 93.3 | 100 |
| 3 | Cat. A | 20 | 94.2 | 29.1 |
| 4 | Cat. A | 48 | 93.5 | 94.7 |
| 5 | Cat. B | 12 | 92.7 | 100 |
| 6 | Cat. C | 20 | 94.8 | 72.6 |
| 7 | Cat. C | 36 | 93.5 | 99.8 |

[a]Hydrogenation was carried out in 0.026 M (dehydronaproxen) MeOH-toluene (2:3, v/v, except for entry 2: MeOH/toluene = 1:3) solution under the following conditions: reaction temperature = 1~2° C.; $P_{H2}$ = 110 kg/cm$^2$; Sub./Cat. = 200 (mol/mol); NEt$_3$/Sub. = 1:1(mol/mol).
[b]Determined by HPLC analysis. Poly-Cat. = polyester-supported [Ru(BINAP)(cymene)Cl$_2$].

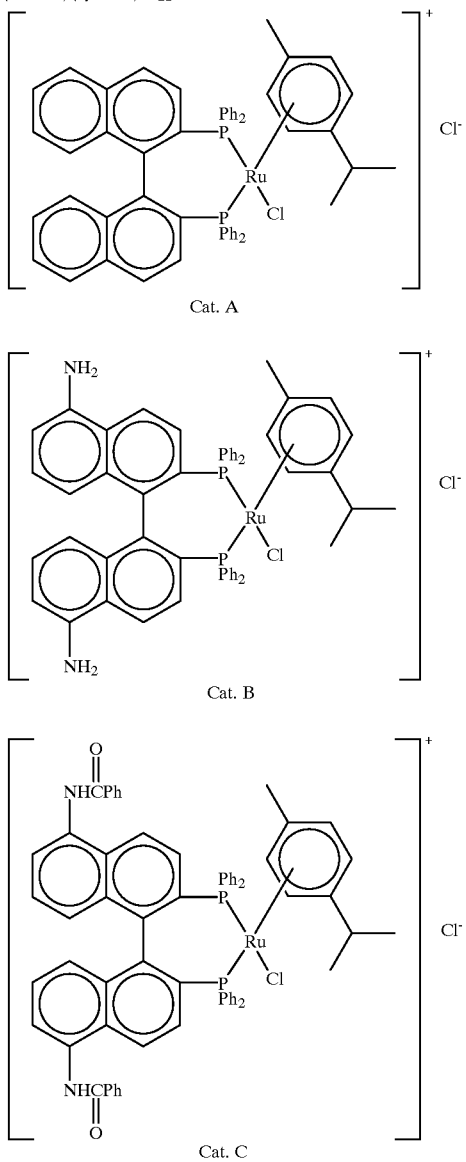

Cat. A

Cat. B

Cat. C

EXAMPLE 12
Asymmetric Hydrogenation of Dehydronaproxen Catalyzed Polyester-Supported [Ru(BINAP)(cymene)Cl$_2$] Catalyst Prepared in situ This example illustrates the recycle of the polyester-supported Ru(BINAP) catalysts:

A 50 mL autoclave with a magnetic stirring bar was charged with 8 mg polyester-supported BINAP ligand (from Example 1), 0.192 mg (3.14×10$^{-4}$ mmol) of [Ru(cymene)Cl$_2$]$_2$ and 3.0 mL of toluene/MeOH (3:2, v/v), and the mixture was premixed for 20 min. 30 mg of dehydronaproxen and 16 μL of NEt$_3$ was then added. The autoclave was then pressurized with hydrogen to 69 kg/cm$^2$ and the mixture was stirred at 25° C. After 5 h of reaction, the autoclave was depressurized and 20 mL cold methanol was added to the reaction mixture. The precipitated polymeric catalyst was collected by filtration and reused for the next reaction. The filtrate was used for the determination of enantiomeric excess and conversion of the product; and the ruthenium measurement was carried out on a PERKIN ELMER Aanalyst 100 atomic absorption spectrometer: measurement at 349.9 nm by using Furnace program. The results are summarized in Table 4.

TABLE 4

| Cycle No. | 0 | 1 | 2 | 3 | 4 | 5 |
|---|---|---|---|---|---|---|
| Time (h) | 5 | 5 | 5 | 5 | 5 | 5 |
| E.e. (%)[b] | 86.0 | 87.6 | 86.0 | 86.3 | 86.3 | 86.1 |
| Conv. (%)[b] | 89.9 | 85.6 | 95.4 | 94.5 | 93.8 | 94.4 |

| Cycle No. | 6 | 7 | 8 | 9 | 10 |
|---|---|---|---|---|---|
| Time (h) | 5 | 5 | 5 | 5 | 5 |
| E.e. (%)[b] | 85.3 | 86.8 | 85.8 | 86.5 | 85.3 |
| Conv. (%)[b] | 95.0 | 82.7 | 95.4 | 93.5 | 96.2 |

[a]Hydrogenation was carried out in 0.084M solution of dehydronaproxen (0.21 mmol in a toluene-methanol mixture, 2.5 mL, v/v = 3:2); H$_2$ = 69.0 kg/cm$^2$; r.t.; Sub./Cat. = 200 (mol/mol); NEt$_3$/Sub. = 1:1 (mol/mol); Catalyst was separated by addition of 20 mL of cold methanol to the catalytic mixture to precipitated the catalyst, filtration and reuse;
[b]Determined by HPLC analysis.

Metal Leaching measurement showed the ruthenium content in the reaction filtrate was below 1.6 ppb (detection limit=1.6 ppb).

EXAMPLE 13
Asymmetric Hydrogenation of Methyl (Z)-2-Acetamidocinnamate Catalyzed by Poly(alkylene tartrate)-Supported [Rh(BPPM)(COD)]$^+$BF$_4^-$ Catalyst (1) Preparation of in-situ catalysts. [Rh(COD)Cl]$_2$ (purchased from Stream Chemicals, Inc., Newburyport, Mass.) (5.0 mg, 0.01 mmol) and AgBF$_4$ (4.0 mg, 0.03 mmol) in THF (2 mL) were stirred at room temperature for 30 minutes under nitrogen atmosphere. The solution was filtered to remove the solid AgCl. After the addition of 110 mg of poly(alkylene tartrate)-supported BPPM (from Example 5) in THF (3 mL) to the solution, poly(alkylene tartrate)-supported [Rh(BPPM) (COD)]$^+$BF$_4^-$ in THF was obtained in situ (4×10$^{-6}$ mol(Rh)/mL).

(2) Asymmetric hydrogenation. A THF solution of the above poly(alkylene tartrate)-supported [Rh(BPPM)(COD)]$^+$BF$_4^-$ (600 μL, 0.0024 mmol) and methyl (Z)-2-acetamidocinnamate (0.053 g, 0.24 mmol) in THF/MeOH (v/v=1:1, 10 mL) were charged to a 50 mL autoclave. The hydrogenation was carried out under 35 kg/cm$^2$ of hydrogen pressure at room temperature for 12 h. A portion of the reaction mixture was analyzed by gas chromatography to determine the product composition. 100% conversion of the starting material to the hydrogenation product and 56.8% e.e. of methyl (R)-2-acetamido-3-phenylpropionate were observed. Activated carbon (5 mg) was added to the solution and the mixture was stirred for 15 minutes. After filtration, the THF solvent was evaporated to give a white solid of methyl (R)-2-acetamido-3-phenylpropanoate (0.050 g), yield 95% and 56.8% e.e. (The enantiomeric excess was determined by chiral capillary GC using a 25 m×0.25 mm Chrompack Chirasil-L-Val column, available from CHROMPACK, Inc. of New Jersey.)

EXAMPLE 14

Asymmetric Hhydrogenation of Methyl (Z)-2-Acetamidocinnamate Catalyzed by Polyester-Supported [Rh (DEGPHOS)(COD)]$^+$BF$_4^-$ Catalyst (1) Preparation of in-situ catalysts. [Rh(COD)Cl]$_2$ (purchased from Stream Chemicals, Inc., Newburyport, Mass.) (5.0 mg, 0.01 mmol) and AgBF$_4$ (4.0 mg, 0.03 mmol) in THF (2 mL) were stirred at room temperature for 30 minutes under nitrogen atmosphere. The solution was filtered to remove the solid AgCl. After the addition of 60 mg of chiral polyester-supported DEGPHOS (from Example 4) in THF (3 mL) to the solution, polyester-supported [Rh (DEGGPHOS) (COD)]$^+$BF$_4^-$ in THF was obtained in situ ($4\times10^{-6}$ mol(Rh)/mL).

(2) Asymmetric hydrogenation. The hydrogenation was carried out via a similar procedure as in example 13 using the above soluble chiral polyester-supported [Rh (DEGPHOS)(COD)]$^+$BF$_4^-$ instead of poly(alkylene tartrate)-supported [Rh(BPPM)(COD)]$^+$BF$_4^-$ (prepared in example 13) to give the product (R)-2-acetamido-3-phenylpropionate, 97% yield and 90.3% e.e. (The enantiomeric excess was determined by chiral capillary GC using a 25 m×0.25 mm Chrompack Chirasil-L-Val column, available from CHROMPACK, Inc. of New Jersey.)

EXAMPLE 15

Asymmetric Hydrogenation of (Z)-2-Acetamidocinnamic Acid Catalyzed by Chiral Polyester-Supported [Rh (DEGPHOS)(COD)]$^+$BF$_4^-$ Catalyst (1) Asymmetric hydrogenation. A THF solution of chiral polyester-supported [Rh(DEGGPHOS)(COD)]$^+$BF$_4^-$ (600 μL, 0.0024 mmol) (prepared as in example 14) and (Z)-2-acetamidocinnamic acid (0.049 g, 0.24 mmol) in 1:1 methanol/THF (10 mL) were charged to a 50 mL autoclave. The hydrogenation was carried out under 35 kg/cm$^2$ of hydrogen pressure at room temperature for 60 minutes.

(2) Recycle of the catalyst. After the H$_2$ was vented, cold methanol (30 mL) was then added to the reaction mixture to precipitate the polymer-supported catalyst [the polyester-supported [Rh(DEGPHOS) (COD)]$^+$BF$_4^-$ catalyst was recovered in>98% yield]. The precipitated polymer-supported catalyst was collected by filtration and reused for the next reaction. The filtrate was used for the determination of enantiomeric excess and conversion of the product [Complete conversion (100%) of the starting material to the hydrogenation product and 96.8% e.e. of (R)-2-acetamido-3-phenylpropionic acid were observed]. The recycled catalyst gave the same activity and enantioselectivity as the freshly prepared catalyst. (The enantiomeric excess was determined by chiral capillary GC using a 25 m×0.25 mm Chrompack Chirasil-L-Val column, which is available from CHROMPACK after converting the product to methyl ester.)

We claim:

1. A polymer-supported chiral phosphine comprising a chiral phosphine ligand immobilized on a soluble polyester support.

2. The polymer-supported chiral phosphine according to claim 1, wherein said soluble polyester support is prepared through polycondensation of a diol with a diacid or a diacid halide.

3. The polymer-supported chiral phosphine according to claim 2, wherein said soluble polyester support comprises a soluble chiral polyester.

4. The polymer-supported chiral phosphine according to claim 1, wherein said chiral phosphine ligand is selected from the group consisting of chiral phosphines containing at least one functional group.

5. The polymer-supported chiral phosphine according to claim 4, wherein said chiral phosphine ligand is selected from the group consisting of chiral hydroxyphosphines or chiral aminophosphines.

6. The polymer-supported chiral phosphine according to claim 4, wherein said chiral phosphine ligand is selected from the group consisting of:

(a) optically active bisphosphine binaphthyl compounds of the formula:

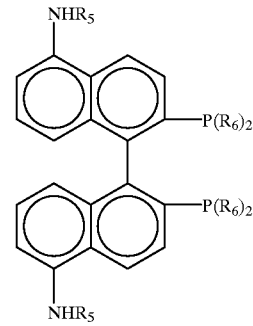

wherein:

i) R$_5$ represents a hydrogen atom, a straight or branched chain alkyl group having 1 to 6 carbon atoms, or a straight or branched chain alkoxy group having from 1 to 6 carbon atoms, or a carbocyclic aromatic group having from 6 to 14 carbon atoms, or an alkyl or alkoxy group as defined above which is substituted by a carbocyclic aromatic group as defined above.

ii) R$_6$ is chosen from the following groups:

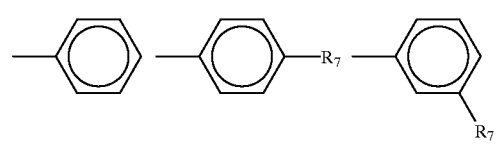

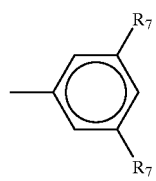

wherein R$_7$ is selected from the group consisting of straight or branched chain alkyl groups having 1 to 6 carbon atoms, and straight or branched chain alkoxy groups having from 1 to 6 carbon atoms;

(b) optically active bisphosphine biphenyl or bipyridyl compounds of the formula:

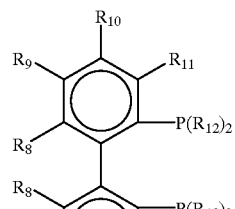

or

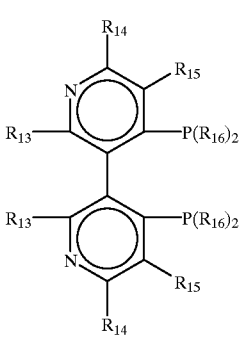

wherein:
i) $R_8$ and $R_{13}$ are independently selected from the group consisting of straight or branched chain alkyl groups having 1 to 6 carbon atoms, and straight or branched chain alkoxy groups having from 1 to 6 carbon atoms;
ii) $R_9$, $R_{10}$, and $R_{11}$ are independently selected from the group consisting of hydrogen atoms, hydroxy groups, amino groups, straight or branched chain alkyl groups having 1 to 6 carbon atoms, and straight or branched chain alkoxy groups having from 1 to 6 carbon atoms, with the proviso that at least one of $R_9$, $R_{10}$, and $R_{11}$ is a hydroxy group or an amino group;
iii) $R_{14}$ and $R_{15}$ are independently selected from the group consisting of hydrogen atoms, hydroxy groups, amino groups, straight or branched chain alkyl groups having 1 to 6 carbon atoms, and straight or branched chain alkoxy group having from 1 to 6 carbon atoms, with the proviso that at least one of $R_{14}$ and $R_{15}$ is a hydroxy group or an amino group;
iv) $R_{12}$ and $R_{16}$ are independently selected from the following groups:

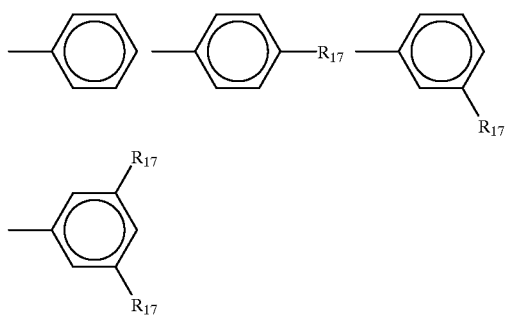

wherein $R_{17}$ is selected from the group consisting of straight or branched chain alkyl groups having 1 to 6 carbon atoms, and straight or branched chain alkoxy group having from 1 to 6 carbon atoms;

(c) optically active bisphosphine ferocenyl compounds of the formula:

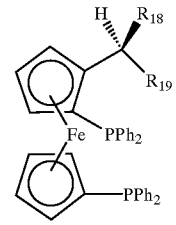

wherein:
i) $R_{18}$ is selected from the group consisting of straight or branched chain alkyl groups having 1 to 6 carbon atoms, and straight or branched chain alkoxy groups having from 1 to 6 carbon atoms; and
ii) $R_{19}$ is selected from the group consisting of hydroxy groups and substituents of formula $N(R_{20})_2$, said substituent of formula $N(R_{20})_2$ being selected from the following groups:

$NMe(CH_2)_2OH$, $NH(CH_2)_2OH$, $N[(CH_2)_2OH]_2$, $NMeCH(CH_2OH)_2$, $NH[CH_2CMe_2OH]$, $NH(CH_2)_3OH$, $NH(CH_2)_2O(CH_2)_2OH$, $NMeC(CH_2OH)_3$, $1,2\text{—}NH\text{—}C_6H_4\text{—}OH$,

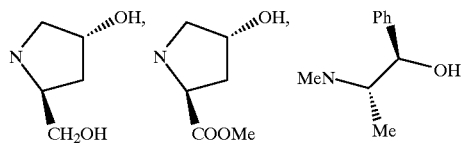

(d) optically active bisphosphine pyrrolidinyl compounds of the formula:

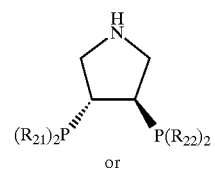

or

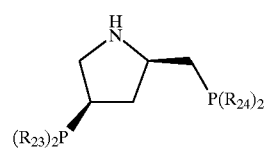

wherein $R_{21}$, $R_{22}$, $R_{23}$ and $R_{24}$ are independently selected from the group consisting of a cycloalkyl group having from 4 to 8 carbon atoms and aryl group, said aryl group being selected from the following groups:

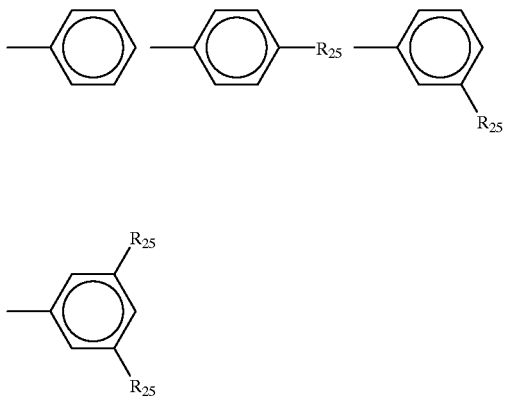

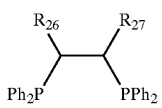

or

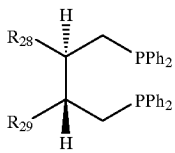

wherein:
i) $R_{26}$ and $R_{28}$ are the same or different and each represents a group of formula —$(CH_2)_r$OH wherein r is an integer of from 0 to 8;
ii) $R_{27}$ is the same as $R_{26}$ or is selected from the group consisting of hydrogen atoms, or a straight or branched chain alkyl groups having 1 to 6 carbon atoms, and straight or branched chain alkoxy groups having from 1 to 6 carbon atoms; and
iii) $R_{29}$ is the same as $R_{28}$ or is selected from the group consisting of hydrogen atoms, straight or branched chain alkyl groups having 1 to 6 carbon atoms, and straight or branched chain alkoxy groups having from 1 to 6 carbon atoms.

7. The polymer-supported chiral phosphine according to claim 6 wherein the chiral phosphine ligand is (S)-5,5'-diamino-2,2'-bis(diphenylphosphino)-1,1'-binaphthyl:

wherein $R_{25}$ is selected from the group consisting of straight or branched chain alkyl groups having 1 to 6 carbon atoms, and straight or branched chain alkoxy groups having from 1 to 6 carbon atoms; and
(e) optically active bisphosphine compounds of the formula:

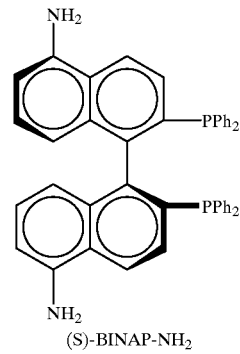
(S)-BINAP-NH$_2$

8. The polymer-supported chiral phosphine according to claim 6 wherein the chiral phosphine ligand is (R)-5,5'-diamino-2,2'-bis(diphenylphosphino)-1,1'-binaphthyl:

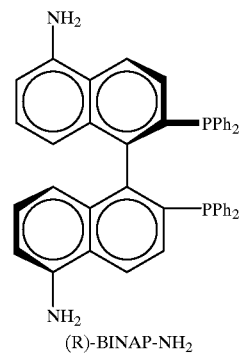
(R)-BINAP-NH$_2$

9. A process for the preparation of the soluble polyester-supported chiral phosphine according to claim 1 comprising copolymerizing a monomeric chiral phosphine with at least one functional group, with a diol and a diacid or a diacid halide.

10. A process for the preparation of the soluble polyester-supported chiral phosphine according to claim 1 comprising reacting a chiral phosphine having at least one functional group, with a soluble polyester prepared through polycondensation of a diol with a diacid or a diacid halide.

11. The process according to claim 9 for the preparation of said soluble polyester-supported chiral phosphine comprising copolymerizing a monomeric chiral phosphine having at least one functional group, with a diol and a diacid chloride.

12. The process according to claim 11 for the preparation of said soluble polyester-supported chiral phosphine comprising copolymerizing (S)- or (R)-5,5'-diamino-2,2'-bis(diphenylphosphino)-1,1'-binaphthyl with a diol and a diacid chloride.

13. The process according to claim 12 for the preparation of said soluble polyester-supported chiral phosphine comprising copolymerizing (S)- or (R)- 5,5'-diamino-2,2'-bis (diphenylphosphino)-1,1'-binaphthyl with a chiral diol and an aromatic diacid chloride, said aromatic diacid chloride being selected from the group consisting of terephthaloyl chloride, isophthaloyl chloride, 4,4'-biphenyldicarbonyl chloride, 4,4'-oxydi-(benzoyl chloride) and 2,6-naphthalene-dicarbonyl chloride.

14. A polyester-supported metal-ligand complex catalyst comprising a metal complexed with the soluble polyester-supported chiral phosphine ligand according to claim 1.

15. The polyester-supported metal-ligand complex catalyst according to claim 14 wherein said metal is selected from a Group VIII of the periodic table of elements.

16. The polyester-supported metal-ligand complex catalyst according to claim 15 wherein said Group VIII metal is selected from rhodium and ruthenium.

17. The polyester-supported metal-ligand complex catalyst according to claim 16 wherein said complex is selected from the group of compounds represented by the general formula $Ru(PP)(X)_s(Y)_t$ wherein: PP represents a soluble polyester-supported chiral phosphine ligand; X and Y are independently selected from the group consisting of benzene groups, p-cymene groups, chelating or non-chelating anionic ligands; s is an integer of 1 or 2; and t is an integer determined according to the formula t=2−s.

18. The polyester-supported metal-ligand complex catalyst according to claim 17 wherein said chelating and non-chelating anionic ligands are selected from the group consisting of chloride, bromide, iodide, tetrafluoroborate, hexafluorophosphate, carboxylate and diketonate ions.

19. The polyester-supported metal-ligand complex catalyst according to claim 17 wherein said catalyst is selected from:
(xix) a group of compounds represented by the general formula $[Ru(PP)(arene)X']^+(Y')^-$, where PP is previously defined, said arene group is selected from benzene and p-cymene groups, and X' and Y' are independently selected from the group consisting of chlorine, bromine and iodide ions;
(xx) a group of compounds represented by the general formula $[Ru(PP)(OAc)_2]$, wherein PP is previously defined and OAc represents an acetoxy group; and
(xxi) a group of compounds represented by the general formula $[Ru(PP)(acac)_2]$, where PP is previously defined and acac represents an acetoacetate group.

20. A polyester-supported metal-ligand complex catalyst wherein said catalyst is selected from:
(xx) a group of compounds represented by the general formula $[Ru(PP')(arene)X']^+(Y')^-$, where PP' represents a soluble polyester-supported chiral phosphine obtained by the process of claim 12, said arene group is selected from benzene and p-cymene groups, and X' and Y' are independently selected from the group consisting of chlorine, bromine and iodide ions;
(xxi) a group of compounds represented by the general formula $[Ru(PP')(OAc)_2]$, where PP' is previously defined, and OAc represents an acetoxy group; and
(xxii) a group of compounds represented by the general formula $[Ru(PP')(acac)_2]$, where PP' is previously defined, and acac represents an acetoacetate group.

21. A polyester-supported metal-ligand complex catalyst wherein said catalyst is selected from:
(xxi) a group of compounds represented by the general formula $[Ru(PP'')(arene)X']^+(Y')^-$, where PP' represents a soluble polyester-supported chiral phosphine obtained by the process of claim 13, said arene group is selected from benzene and p-cymene groups, and X' and Y' are independently selected from the group consisting of chlorine, bromine and iodide ions;
(xxii) a group of compounds represented by the general formula $[Ru(PP')(OAc)_2]$, where PP' is previously defined, and OAc represents an acetoxy group; and
(xxiii) a group of compounds represented by the general formula $[Ru(PP'')(acac)_2]$, where PP'' is previously defined, and acac represents an acetoacetate group.

22. The polyester-supported metal-ligand complex catalyst according to claim 16 wherein said catalyst is selected from a group of compounds represented by the general formula $[Rh(COD)(PP)]X''$ where PP represents a soluble polyester-supported chiral phosphine ligand, COD represents a cyclooctadiene and X'' represents a balancing anion.

23. The polyester-supported metal-ligand complex catalyst according to claim 22 wherein said balancing anion is selected from the group consisting of chloride, bromide, iodide, tetrafluoroborate, hexafluorophosphate, perchlorate and tetraphenylborate anions.

24. A hydrogenation process comprising reacting a prochiral compound with hydrogen in the presence of a soluble polyester-supported metal-ligand complex catalyst according to claim 14 to produce an optically active hydrogenation product.

25. The hydrogenation process according to claim 24 comprising hydrogenation of an optionally substituted olefin in the presence of a soluble polyester-supported metal-ligand complex catalyst, the catalyst comprising a metal complexed with a soluble polyester-supported chiral phosphine ligand.

26. The hydrogenation process according to claim 25 wherein said olefin is an unsaturated carboxylic acid.

27. The hydrogenation process according to claim 26 wherein said unsaturated carboxylic acid compound is a 2-arylpropenoic acid, and said aryl group is selected from the following groups:

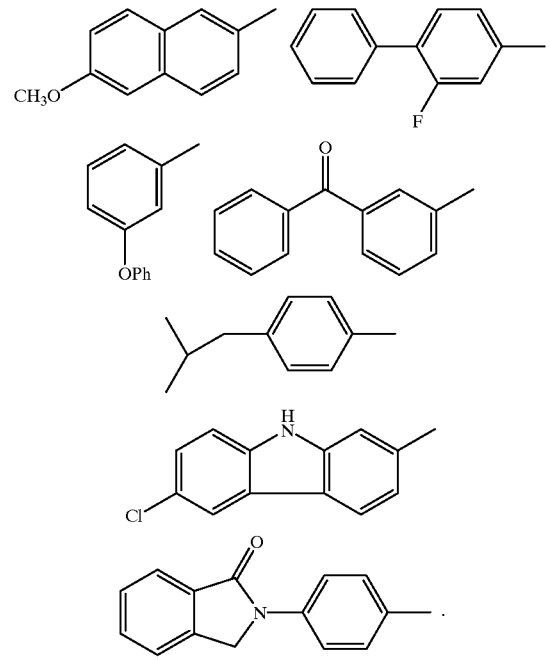

28. A hydrogenation process comprising hydrogenation of 2-(6'-methoxyl-2'-naphthyl)propenoic acid in the presence of the soluble polyester-supported Ru(BINAP) catalyst according to claim 20, to produce naproxen.

29. A hydrogenation process comprising hydrogenation of 2-(6'-methoxyl-2'-naphthyl)propenoic acid in the presence of the soluble polyester-supported Ru(BINAP) catalyst according to claim 21, to produce naproxen.

30. The hydrogenation process according to claim 25 comprising hydrogenation of an olefin selected from the group consisting of α-amidoacrylic acids, (Z)-α-benzamidocinnamic acid and (Z)-α-benzamido-β-(4-hydroxy-3-methoxy- phenyl)acrylic acid.

31. The hydrogenation process according to claim 24 comprising hydrogenation in a homogeneous manner at a hydrogen pressure from 1 to 150 kg/cm$^2$ and a temperature of from −10° C. to 100 ° C., the molar ratio of said prochiral compound to said soluble polyester-supported catalyst (calculated in terms of the amount of transition metal present in said catalyst) being from 100 to 100,000.

32. The hydrogenation process according to claim 24 wherein said soluble polyester-supported catalyst is recycled, and the recycled catalyst thus obtained has essentially the same reactivity and enantioselectivity as the freshly prepared catalyst.

33. The hydrogenation process according to claim 24 wherein said soluble polyester-supported catalyst is isolated after reaction via a method selected from the group consisting of temperature change, selective precipitation and differential solubility.

34. The process according to claim 33 wherein said soluble polyester-supported catalyst is isolated after reaction via selective precipitation upon the addition of an alcoholic solvent to the reaction mixture.

* * * * *